United States Patent [19]

Quallich

[11] Patent Number: 5,196,607
[45] Date of Patent: Mar. 23, 1993

[54] PROCESS FOR PREPARING KETONE ENANTIOMER

[75] Inventor: George J. Quallich, North Stonington, Conn.

[73] Assignee: Pfizer Inc., New York, N.Y.

[21] Appl. No.: 837,012

[22] Filed: Feb. 14, 1992

[51] Int. Cl.$^5$ .................. C07C 45/41; C07C 45/46
[52] U.S. Cl. ................... 568/327; 570/184; 558/388; 568/319; 568/322; 568/323; 568/338; 568/809
[58] Field of Search ............... 568/319, 322, 323, 327, 568/328, 338

[56] References Cited

U.S. PATENT DOCUMENTS

| | | | |
|---|---|---|---|
| 4,536,518 | 8/1985 | Welch, Jr. et al. | 514/647 |
| 4,556,676 | 12/1985 | Welch, Jr. et al. | 514/554 |
| 4,777,288 | 10/1988 | Quallich et al. | 562/491 |
| 4,839,104 | 6/1989 | Quallich et al. | 260/396 R |

OTHER PUBLICATIONS

W. M. Welch Jr. et al., *In The Journal of Medicinal Chemistry*, vol. 27, No. 11, (1984); pp. 1508–1519.
T. Mukaiyama et al., in *Chemistry Letters*, pp. 913–916, (1981).

*Primary Examiner*—Joseph Paul Brust
*Attorney, Agent, or Firm*—Peter C. Richardson; Paul H. Ginsburg

[57] ABSTRACT

A novel multi-step process for preparing the (4S)-enantiomer of 4-(3,4-dichlorophenyl)-3,4-dihydro-1(2H)-naphthalenone in a highly-optically pure form is disclosed. The process involves (1) first reacting 3,4-dichlorocinnamyl chloride with L-(-)-ephedrine in a chlorinated lower hydrocarbon solvent to form the corresponding chiral N-methyl-N-(β-hydroxy-β-phenylisopropyl)-3-(3,4-dichlorophenyl)propenoamide; (2) then subjecting the chiral α,β-unsaturated amide formed in the first step to a Grignard reaction with phenyl magnesium chloride or bromide, followed by hydrolysis, to effect a conjugate addition of the phenyl group and the hydrogen element to the aforesaid α,β-unsaturated propenoamide and so selectively form the corresponding chiral N-methyl-N-(β-hydroxy-β-phenylisopropyl)-3-(3,4-dichlorophenyl)-3-phenyl-propanoamide; (3) hydrolyzing the aforesaid chiral 3-phenylated propanoamide compound to yield the corresponding 3-(3,4-dichlorophenyl)-(3R)-propanoic acid; (4) next esterifying the stereospecific (3R)-phenylated propanoic acid obtained in the third step with an appropriate lower alkanol in the presence of thionyl chloride or a lower alkanoyl chloride to form the corresponding lower alkyl 3-(3,4-dichlorophenyl)-(3R)-phenylpropanoate; (5) then reducing the stereospecific (3R)-phenylated propanoic acid ester with an appropriate carbonyl reducing agent to form the desired 3-(3,4-dichlorophenyl)-(3R)-phenylpropanol intermediate; (6) then chlorinating the stereospecific (3R)-phenylated n-propanol compound to afford the corresponding 3-(3,4-dichlorophenyl)-(3R)-phenylpropyl chloride; (7) next reacting the stereospecific (3R)-phenylated n-propyl chloride with an alkali metal cyanide to form the corresponding 4-(3,4-dichlorophenyl)-(4R)-phenylbutyronitrile; (8) and then hydrolyzing the stereospecific (4R)-phenylated butyronitrile compound to form the corresponding 4-(3,4-dichlorophenyl)-(4R)-phenylbutanoic acid; and (9) thereafter converting the stereospecific (4R)-phenylated n-butanoic acid compound to the corresponding 4-(3,4-dichlorophenyl)-(4R)-phenylbutanoyl chloride by treatment with thionyl chloride, followed cyclization of the aforesaid butanoyl chloride compound in the presence of a Friedel-Crafts type catalyst to finally yield the corresponding (4S)-4-(3,4-dichlorophenyl)-3,4-dihydro-1(2H)-naphthalenone enantiomer in the desired isomer weight ratio in the resultant isomeric product mixture that allows for the recovery of said individual isomer therefrom in a highly optically-pure form. The desired (4S)-enantiomer has utility as an intermediate that ultimately leads to pure cis-(1S)(4S)-N-methyl-4-(3,4-dichlorophenyl)-1,2,3,4-tetrahydro-1-naphthaleneamine (sertraline), which is a known antidepressant agent. The aforementioned 3-(3,4-dichlorophenyl)-(3R)-phenylpropyl alcohol and chloride compounds, as well as the corresponding 4-(3,4-dichlorophenyl)-(4R)-phenylbutyronitrile, are all novel products per se, which are useful as key intermediates in the overall process of the present invention.

15 Claims, No Drawings

PROCESS FOR PREPARING KETONE ENANTIOMER

BACKGROUND OF THE INVENTION

This invention relates to a new and useful process for preparing a ketone enantiomer. More particularly, it is concerned with a novel multi-step process for preparing the (4S)-enantiomer of 4-(3,4-dichlorophenyl)-3,4-dihydro-1(2H)-naphthalenone in a highly optically-pure form. The latter compound, which is a novel (4S)-enantiomer per se, has utility as a key intermediate that ultimately leads to the production of pure cis-(1S)(4S)-N-methyl-4-(3,4-dichlorophenyl)-1,2,3,4-tetrahydro-1-naphthaleneamine (sertraline), which is a known antidepressant agent. The invention also includes within its scope certain other novel compounds which are useful as intermediates in the various stages of the overall process.

There is described in U.S. Pat. Nos. 4,536,518 and 4,556,676 to W. M. Welch, Jr. et al., as well as in the paper of W. M. Welch, Jr. et al., appearing in the *Journal of Medicinal Chemistry*, Vol. 27, No. 11, p. 1508 (1984), a multi-step method for synthesizing pure racemic cis(1S)(4S)-N-methyl-4-(3,4-dichlorophenyl)-1,2,3,4-tetrahydro-1-naphthaleneamine, starting from the readily available 3,4-dichlorobenzophenone and proceeding via the known racemic or (±)-4-(3,4-dichlorophenyl)-4-butanoic acid and then to (±)-4-(3,4-dichlorophenyl)-3,4-dihydro-1(2H)-naphthalenone (see also U.S. Pat. Nos. 4,777,288 and 4,839,104 to G. J. Quallich et al. for improved methods leading to these intermediates), with the latter ketone then being condensed with methylamine in the presence of titanium tetrachloride to yield N-[4-(3,4-dichlorophenyl)-3,4-dihydro-1(2H)-naphthalenylidene]methenamine. In the last step of the overall synthesis, the aforementioned imine is then readily reduced by means of catalytic hydrogenation or by the use of a metal hydride complex to yield N-methyl-4-(3,4-dichlorophenyl)-1,2,3,4-tetrahydro-1-naphthaleneamine, which is actually a mixture of the cis- and trans-isomers in the form of a racemate. The aforesaid isomeric mixture is then separated into its component parts by conventional means, e.g., by fractional crystallization of the hydrochloride salts or by column chromatography on silica gel of the corresponding free base. Resolution of the separated cis-racemate free base compound while in solution with an optically-active selective precipitant acid, such as D-(−)-mandelic acid, then ultimately affords the desired cis(1S)(4S)-enantiomer (sertraline).

Nevertheless, the above described production of pure cis-(1S)(4S)-N-methyl-4-(3,4-dichlorophenyl)-1,2,3,4-tetrahydro-1-naphthaleneamine (sertraline) is disadvantageous in that equal amounts of the unwanted cis(1R)(4R)-enantiomer are co-produced and must eventually be discarded, thereby lowering the overall yield of the desired cis-(1S)(4S)-enantiomer and increasing the total costs of production.

Other asymmetric methods of induction (e.g., asymmetric synthesis) have been employed in the past with variable success in the field of organo-metallic chemistry to stereoselectively convert (and thereby resolve) other specific substrates. For instance, in a paper by T. Mukaiyama et al., appearing in *Chemistry Letters*, p. 913 (1981), there is described the Michael addition of various Grignard reagents, such as n-butylmagnesium bromide, to certain chiral α,β-unsaturated carboxylic acid amides that are derived from L-(−)-ephedrine (e.g., the corresponding crotonic acid amide) to yield the corresponding highly optically-active β-substituted alkanoic acids, like (S)-3-methylheptanoic acid, after acid hydrolysis. In those instances where an aromatic Grignard reagent, such as phenylmagnesium bromide, was employed as the reagent, the corresponding chiral product obtained (i.e., the highly optically-active β-substituted phenylpropionic acid) always appeared to be of the (S)-configuration.

SUMMARY OF THE INVENTION

In accordance with the present invention, there is now provided a new and especially useful process for preparing the (4S)-enantiomer of 4-(3,4-dichlorophenyl)-3,-dihydro-1(2H)-naphthalenone in a highly optically-pure form by employing a novel multi-step series of reactions, starting from the known 3,4-dichlorocinnamyl chloride. More particularly, the novel process of this invention comprises a sequential series of steps that involve:

(a) first reacting 3,4-dichlorocinnamyl chloride with at least an equimolar amount of L-(−)-ephedrine in a chlorinated lower hydrocarbon solvent at a temperature ranging from about −20° C. up to about 25° C. to form the corresponding chiral N-methyl-N-(β-hydroxy-β-phenylisopropyl)-3-(3,4-dichlorophenyl)-propenoamide;

(b) subjecting the chiral unsaturated amide product obtained in step (a) to a Grignard reaction with a large excess in moles of phenyl magnesium chloride or bromide in a cyclic or lower dialkyl ether at a temperature ranging from about −80° C. up to about 25° C., followed by hydrolysis, to effect a conjugate addition of the phenyl group and the hydrogen element to the aforesaid α,β-propenoamide and so selectively form the corresponding chiral N-methyl-N-(β-hydroxy-B-phenylisopropyl)-3-(3,4-dichlorophenyl)-3-phenyl-propanoamide;

(c) hydrolyzing the aforesaid chiral 3-phenylated propanoamide product of step (b) in a lower alkylene glycol solvent in the presence of an alkali metal hydroxide as base to form the corresponding 3-(3,4-dichlorophenyl)-(3R)-phenylpropanoic acid;

(d) esterifying the stereospecific (3R)-phenylated propanoic acid obtained in step (c) with an appropriate lower alkanol in the presence of thionyl chloride or a lower alkanoyl chloride to form the corresponding lower alkyl 3-(3,4-dichlorophenyl)-(3R)-phenyl-propanoate;

(e) reducing the stereospecific (3R)-phenylated propanoic acid ester of step (d) with an appropriate carbonyl reducing agent in a reaction-inert polar aprotic organic solvent at a temperature ranging from about 0° C. up to about 100° C. until the reduction to form the desired 3-(3,4-dichlorophenyl)-(3R)-phenylpropanol intermediate is substantially complete;

(f) chlorinating the stereospecific (3R)-phenylated n-propanol compound obtained in step (e) with carbon tetrachloride in an excess of said reagent as solvent and in the presence of triphenylphosphine at a temperature of from about 50° C. up to about the reflux temperature of the reaction mixture to form the corresponding 3-(3,4-dichlorophenyl)-(3R)-phenylpropyl chloride;

(g) reacting the stereospecific (3R)-phenylated n-propyl chloride obtained in step (f) with an alkali metal cyanide in a reaction-inert polar organic solvent at reflux temperatures to form the corresponding 4-(3,4-dichlorophenyl)-(4R)-phenylbutyronitrile;

(h) hydrolyzing the stereospecific (4R)-phenylated butyronitrile product of step (g) in a lower alkylene glycol solvent in the presence of an alkali metal hydroxide as base to form the corresponding 4-(3,4-dichlorophenyl)-(4R)-phenylbutanoic acid; and (i) thereafter converting the stereospecific phenylated n-butanoic acid compound obtained in step (h) to the corresponding 4-(3,4-dichlorophenyl)-(4R)-phenylbutanoyl chloride by treatment with thionyl chloride in a reaction-inert aprotic organic solvent, followed by cyclization of the aforesaid butanoyl chloride compound in the presence of a Friedel-Crafts type catalyst at a temperature ranging from about $-5°$ C. up to about $25°$ C. to finally yield the corresponding (4S)-4-(3,4-dichlorophenyl)-3,4-dihydro-1(2H)-naphthalenone enantiomer in the desired isomer weight ratio in the resultant isomeric product mixture that allows for the recovery of said individual isomer therefrom in a highly optically-pure form and in a high yield.

In this way, a compound such as 3,4-dichlorocinnamyl chloride is readily converted in the form of the corresponding amide derived from L-(−)-ephedrine to the corresponding chiral 3-phenylated propanoamide compound and then to the corresponding stereospecific 3-(3,4-dichlorophenyl)-(3R)-phenylpropanoic acid, which is then converted, via the corresponding (3R)-phenylpropanoic acid lower alkyl ester, to the corresponding novel chiral compounds successively derived therefrom, viz., 3-(3,4-dichlorophenyl)-(3R)-phenylpropanol, 3-(3,4-dichlorophenyl)(3R)-phenylpropyl chloride and 4-(3,4-dichlorophenyl)-(4R)phenylbutyronitrile. The latter compound, in turn, then leads to the novel 4-(3,4-dichlorophenyl)-(4R)-phenylbutanoic acid that ultimately affords the (4S)-enantiomer final product, viz., (4S)-4-(3,4-dichlorophenyl)-3,4-dihydro-1(2H)-naphthalenone. As previously indicated, the latter-named final product is useful as a valuable intermediate in the asymmetric synthesis of the antidepressant agent known as sertraline, which is cis-(IS)-(4S)-N-methyl-4-(3,4-dichlorophenyl)-1,2,3,4-tetrahydro-1-naphthaleneamine [see aforementioned U.S. Pat. No. 4,536,518, as well as the *Journal of Medicinal Chemistry*, Vol. 27, No. 11, p. 1508 (1984), for the total synthesis of the corresponding racemic compound and its subsequent conversion into sertraline].

Accordingly, there is also included within the preview of this invention the novel chiral derivatives of 3-(3,4-dichlorophenyl)-(3R)-phenylpropanoic acid that are used as intermediates in the process, including such derivatives as 3-(3,4-dichlorophenyl)-(3R)-phenylpropanol, 3-(3,4-dichlorophenyl)-(3R)-phenylpropyl chloride and 4-(3,4-dichlorophenyl)-(4R)-phenylbutyronitrile for the present purposes at hand. The latter novel compound, of course, leads directly to the corresponding 4-(3,4-dichlorophenyl)-(4R)-phenylbutanoic acid, which is thereafter cyclized to (4S)-(3,4-dichlorophenyl)-3,4-dihydro-1(2H)-naphthalenone, as previously discussed.

DETAILED DESCRIPTION OF THE INVENTION

In accordance with the process of this invention, the initial stage of the multi-step synthesis for producing the desired (4S)-4-(3,4-dichlorophenyl)-3,4,-dihydro-1(2H)-naphthalenone compound involves first reacting the known 3,4-dichlorocinnamyl chloride in step (a) with at least an equimolar amount of L-(−)-ephedrine in a chlorinated lower hydrocarbon solvent at a temperature ranging from about $-20°$ C. up to about $25°$ C. to form the corresponding chiral N-methyl-N-($\beta$-hydroxy-$\beta$-phenylisopropyl)-3-(3,4-dichlorophenyl)-propenoamide. This reaction is preferably accomplished in the presence of a base, such as an alkali metal hydroxide or an anhydrous tertiary-amine base like pyridine and triethylamine, which ensures complete removal of the hydrogen chloride by-product and so shifts the reaction equilibrium to the right-hand side of the equation (i.e., towards completion). In practice, it is most preferably accomplished by using up to two moles of L-(−)-ephedrine base per mole of acid chloride starting material, thus enabling reaction completion to be achieved in a most efficient and homogeneous manner. Preferred chlorinated lower hydrocarbon solvents for use as reaction media in this connection include methylene chloride, ethylene dichloride, chloroform, trichloroethylene, s-tetrachlorethane and carbon tetrachloride, etc. In general, it has often been found desirable to stir the reaction mixture at non-chilling or even at slightly-elevated temperatures up to about $25°$ C. for a period of at least about one-half hour after mixing of the two reactants is complete, but the latter step per se must always be carried out at chilling temperatures, i.e., at $0°$ C. or even slightly below (e.g., as low as about $-20°$ C.), before allowing the aforesaid warm-up trend to take place. Upon completion of the overall reaction step, the desired chiral $\alpha,\beta$-unsaturated amide product is then easily isolated from the reaction mixture in a most conventional manner, viz., by first washing same with water, dilute acid and then with water again, followed by a saturated aqueous solution of a weak base (in that order), and then drying and evaporating the washed organic solution to ultimately yield the desired chiral amide product. The latter $\alpha,\beta$-unsaturated intermediate can then be further purified by means of recrystallization from isopropyl ether and used as such in the next reaction step.

The chiral $\alpha,\beta$-unsaturated amide product obtained in step (a) is then subjected to a Grignard reaction in step (b) by using a large excess in moles of phenyl magnesium chloride or bromide in a cyclic or lower dialkyl ether at a temperature ranging from about $-80°$ C. up to about $25°$ C., followed by hydrolysis, to effect a conjugate addition of the phenyl group and the hydrogen element to the $\alpha,\beta$-propenoamide and so selectively form the corresponding chiral N-methyl-N-($\beta$-hydroxy-$\beta$-phenylisopropyl)-3-(3,4-dichlorophenyl)-3-phenylpropanoamide. This step represents the Michael addition of a Grignard reagent and was earlier explored by T. Mukaiyama et al., in Chemistry Letters, p. 913 (1981); the latter work involved a study of the corresponding crotonic acid amides. The present reaction step has been carried out essentially in accordance with the T. Murkaijama et al. procedure. Approximately 5 to 7 moles of phenyl magnesium halide reagent are employed per one mole of $\alpha,\beta$-unsaturated amide starting material. Preferred solvents for the reaction include cyclic ethers such as dioxane and tetrahydrofuran, as well as lower dialkyl ether like diethyl ether, di-isopropyl either and 1,2-dimethoxyethane. The mixing step is generally performed at the extreme lower end of the aforesaid temperature range (and most preferably, at about -78° C), while the spent reaction mixture is usually thereafter stirred at temperatures near $0°$ C. for a period of about three days in order to ensure completion of reaction. Upon completion of his step (i.e., the Michael addition of the Grignard reagent), the reaction mixture is next quenched with pH 7 phosphate buffer (which also concomitantly effects hydrolysis to the desired B-substituted chiral amide product) and the resulting reaction mixture is next filtered, and the organic phase of the saved filtrate is then separated and subsequently concentrated in vacuo to afford the desired chiral N-methyl-N-($\beta$-hydroxy-$\beta$-phenylisopropyl)-3-(3,4-dichlorophenyl)-3-phenylpropanoamide product. The latter material is then ready for use in the next reaction step without any further purification being required.

The next step (c) involved in the overall synthetic process of this invention relates to the hydrolysis of the aforesaid chiral 3-phenylated propanoamide product obtained in step (b) to the corresponding 3-(3,4-dichlorophenyl)-(3R)-phenylpropanoic acid. This is effectively achieved by preferably heating the amide under alkaline conditions in a polyhydric alcohol medium for a sufficient period of time until formation of the desired chiral acid is substantially complete. In practice, this amounts to heating the chiral amide in a lower alkylene glycol, i.e., one having from two to four carbon atoms, such as ethylene glycol, 1,2-propylene glycol and 2,3-butylene glycol, in the presence of an alkali metal hydroxide at a temperature ranging from about $-50°$ C. up to about 120° C. for a period of at least about 24 hours. Preferred alkali metal hydroxides for use in this connection include sodium hydroxide and potassium hydroxide, with the latter agent being most preferred. The amount of alkali metal hydroxide to be employed is usually not critical, but it is definitely desirable to use at least an equimolar amount of base with respect to the amide starting material and it is certainly most preferable in practice to employ a large excess in moles of said base (say, for example, up to ten moles of the base with respect to one mole of amide starting material) for the present purposes at hand. Upon completion of this step, the desired product is recovered from the reaction mixture in a most conventional manner, e.g., by first diluting the reaction mixture with water and then adjusting to pH 10 with concentrated hydrochloric acid, followed by extraction of the aqueous phase with diethyl ether and further adjustment of the pH of the thus-extracted aqueous phase to pH 2 with additional concentrated hydrochloric acid. Extraction of the acidic aqueous phase with ethyl acetate, followed by washing of the organic extract with phosphate pH 2 buffer and then drying and evaporating same, etc., yields the desired acid, which can then be further purified by washing an ethereal solution of same with fresh phosphate pH 2 buffer. In this way, pure 3-(3,4-dichlorophenyl)-(3R)-phenylpropanoic acid is finally obtained and this material is now ready for use in the next reaction step (for conversion to the ester) as will hereinafter be described.

The fourth step (d) involves esterifying the stereospecific (3R)-phenylated propanoic acid compound obtained in step (c) with an appropriate lower alkanol ($C_1$-$C_3$) in the presence of thionyl chloride or a lower alkanoyl chloride to form the corresponding lower alkyl 3-(3,4-dichlorophenyl)-3(R)-phenylpropanoate in a most facile manner. This particular reaction step is readily accomplished by any number of convention esterification techniques and most preferably, by contacting the starting chiral acid with an excess of the appropriate lower alkanol of choice (e.g., methanol or ethanol, etc.) as the reactant solvent, and in the presence of a sufficient amount of thionylchloride or acetyl chloride to generate at least a trace amount of the corresponding mineral acid in situ, in accordance with standard Fischer esterification procedure. In practice, the acid halide reagent is first dissolved in the alkanol solvent medium at temperatures ranging from about $-15°$ C. up to about 10° C. to initially form a catalytic amount (e,g., up to about 3% by weight) of the corresponding mineral acid in situ, and the resulting alkanolic mixture containing this catalyst is then added to the organic acid substrate (with constant agitation) and slowly allowed to warm to ambient temperatures, and thereafter stirred and heated to a temperature of up to about 50° C. in order to complete the acid-catalyzed esterification step and so obtain the desired ester. Although time is usually not a critical factor in this reaction, a period of at least about one hour is often considered desirable but this will, of course, vary depending upon whether a higher or lower reaction temperature is employed. Upon completion of this step, the chiral ester so obtained is then easily isolated from the reaction mixture in a conventional manner, e.g., by first concentrating the mixture in vacuo to remove excess alkanol and other volatiles and thereafter dissolving the residue in a non-polar solvent, such as diethyl ether, and washing the latter with water, phosphate pH 9 buffer and brine in that order, prior to drying and evaporating once again. Further purification of the ester product can then be achieved via column chromatography on silica gel, if so desired. In this way, 3-(3,4-dichlorophenyl)-(3R)-phenylpropanoic acid is readily converted, via acid-catalyzed esterification, to pure methyl or ethyl 3-(3,4-dichlorophenyl)-(3R)-phenylpropanoate, etc. and used as such in the next step of the overall process.

The fifth and next step (e) of the multi-step process of this invention involves reducing the stereospecific (3R)-phenylated propanoic acid ester of step (d) with an appropriate carbonyl reducing agent in a reaction-inert polar aprotic organic solvent at a temperature ranging from about 0° C. up to about 100° C. until the reduction reaction to form the corresponding desired 3-(3,4-dichlorophenyl)-(3R)-phenylpropanol intermediate compound is substantially complete. This particular reaction step is readily accomplished by the use of such carbonyl reducing agents as lithium aluminum hydride or a complex oxidizable metal borohydride, such as a complex alkali metal borohydride with aluminum chloride, in accordance with conventional organic procedures, to afford the desired phenylpropanol compound in the form of a complex salt. The latter salt is then subsequently decomposed by means of the addition of water thereto and preferably by adding any commonly-used aqueous system for these purposes, provided that it possesses at least a slightly basic pH in nature, like aqueous disodium tartrate, for example, or even dilute aqueous sodium hydroxide. The initial reduction step is best carried out by using an excess in moles of the carbonyl reducing agent e.g., at least in excess of one mole of the reducing agent in an ethereal solvent system at temperatures that preferably range from about 10° C. up to about 80° C., for the present purposes at hand, i.e., at least up to about the reflux temperature of the reaction mixture if the boiling point of the solvent employed is below the upper limit of the aforesaid range. Preferred ethereal solvents for use in this connection include diethyl ether, di-isopropyl ether, di-n-butyl ether, tetrahydrofuran and dioxane. Although time is not a critical factor in the reaction, it is preferred in practice to carry out the reaction for a period of at least about 15 hours in order to ensure maximum yields. Upon completion of the reduction step, the reaction mixture is next quenched with an aqueous system as aforesaid and the desired product is readily recovered from the resulting ethereal layer by any number of conventional techniques once decomposition of the aforesaid complex salt has already taken place. For instance, the thoroughly washed and dried ethereal layer can be concentrated under reduced pressure to afford the crude product as residual material, which is then purified by such means as column chromatography over silica gel to eventually afford the pure desired intermediate chiral alcohol product, viz., 3-(3,4-dichlorophenyl)-(3R)-phenylpropanol.

The sixth step (f) of the multi-step process of the present invention involves chlorinating the stereospecific (3R)-phenylated n-propanol compound obtained in step (e) with carbon tetrachloride in an excess of said reagent as solvent and in the presence of triphenylphosphine at an elevated temperature to form the corresponding 3-(3,4-dichlorophenyl)-(3R)-phenylpropyl chloride. This particular reaction step is readily accomplished by contacting the 3-(3,4-dichlorophenyl)-(3R)-phenylpropanol starting material in a carbon tetrachloride solvent system with at least an equimolar amount of the triphenylphosphine reagent at a temperature ranging from about 50° C. up to about the reflux temperature of the reaction mixture until the conversion of the starting alcohol to the corresponding propyl chloride compound is substantially complete. In practice, the chlorination step is preferably conducted by heating the reactants together at a temperature at or near the reflux temperature of the reaction mixture for a period of at least about one hour and usually by using a slight excess in moles of the triphenylphosphine reagent. Upon completion of this step, the desired product is easily recovered from the cooled reaction mixture by first diluting same with equal volumes of 5% aqueous sodium sulfate and chloroform, followed by the successive drying and concentration (in vacuo) of the resulting combined organic extracts and subsequent purification of the residue (i.e., the residual oil) by means of column chromatography on silica gel to effectively yield the desired new chiral chloro compound, viz., 3-(3,4-dichlorophenyl)-(3R)-phenylpropyl chloride, in substantially pure form and ready for use in the next step of the overall reaction process.

The seventh and next step (g) of the overall process of this invention involves reacting the stereospecific (3R)-phenylated n-propyl chloride compound obtained in step (f) with an alkali metal cyanide, like sodium or potassium cyanide, in a reaction-inert polar protic or aprotic organic solvent at or near reflux temperatures to form the corresponding 4-(3,4-dichlorophenyl)-(4R)-phenylbutyronitrile. This particular reaction step is readily accomplished by heating the two reactants together at or near reflux temperatures in the aforesaid solvent system until the metathetical reaction to form the desired nitrile product is substantially complete. In practice, this usually entails using a moderate excess in moles of the cyanide reagent with respect to chloride starting material, so that the ratio in moles of cyanide reagent to chloride starting material generally lies in the range of from about 1.25:1.0 up to about 3.0:1.0 for the present purposes at hand. It has also been found most convenient in practice (and may even be most desirable) to employ a catalytic amount of a crown ether like 1,4,7,10,13,16-hexaoxacyclooctadecane, in order to ensure completeness of reaction. A preferred catalytic amount of such a reagent would generally be of the order of about one-tenth the molar amount of the aforesaid starting material. Preferred reaction-inert polar protic organic solvents for use with the reaction include the lower alkanols such as methanol, ethanol and isopropanol, while preferred reaction-inert polar aprotic organic solvents include acetonitrile and the lower N,N-dialkyl lower alkanoamides such as dimethylformamide, diethylformamide, dimethylacetamide and the like. The reaction time is not a critical factor and will vary somewhat with the individual solvent employed, at least insofar as those having a lower boiling point will generally require longer reaction times than do those having a higher boiling point. In general, a reaction time of at least about four hours is usually required in order to ensure completeness of reaction. Upon completion of the aforesaid reaction step, the desired chiral nitrile product is easily isolated from the spent reaction mixture in a most convenient fashion. For instance, the cooled mixture is first diluted with water and then extracted with chloroform, followed by the usual washing and drying of the saved organic layers (in combination) and then the eventual concentration of the latter under reduced pressure to yield a residual oil. Further purification of the crude product is then achieved via column chromatography on silica gel and there is finally obtained the pure desired novel chiral nitrile compound designated as 4-(3,4-dichlorophenyl)-(4R)-phenylbutyronitrile.

The eighth and next-to-last step (h) of the overall multi-step process of the present invention involves hydrolyzing the stereospecific (4R)-phenylated butyronitrile product of step (g) in a lower alkylene glycol solvent in the presence of an alkali metal hydroxide as base to form the corresponding 4-(3,4-dichlorophenyl)-(4R)-phenylbutanoic acid. This reaction step is preferably achieved by heating the chiral nitrile in a lower alkylene glycol having from two to four carbon atoms, such as ethylene glycol, 1,2-propylene glycol and butylene glycol, etc., in the presence of an alkali metal hydroxide like sodium hydroxide or potassium hydroxide, at a temperature ranging from about 5° C. up to about 120° C. for a period of at least about five hours. The amount of alkali metal hydroxide employed as base is not critical, but it is desirable to use at least an equimolar amount of said base with respect to the nitrile starting material. In practice, it is certainly most preferable to employ a large excess in moles of said base with respect to the nitrile starting material (say, for example, up to about ten moles of the base per one mole of the nitrile) for the present purposes at hand. Upon completion of this step, the desired chiral acid product is recovered from the reaction mixture in a conventional manner, viz., by employing essentially the same procedures previously described for the chiral amide product of step (c). In this way, pure 4-(3,4-dichlorophenyl)-(4R)-phenylbutanoic acid is readily obtained and this material is now ready for use in the last step of the overall process.

The ninth and final step (i) of the multi-step process of this invention involves converting the stereospecific (4R)-phenylated n-butanoic acid compound obtained in step (h) to the corresponding 4-(3,4-dichlorophenyl)-(4R)-phenylbutanoyl chloride by treatment with thionyl chloride in a reaction-inert aprotic organic solvent, followed by cyclization of the aforesaid butanoyl chloride compound in the presence of a Friedel-Crafts type catalyst at a temperature ranging from about −5° C. up to about 25° C. to finally yield the corresponding (4R)-4-(3,4-dichlorophenyl)-3,4-dihydro-1(2H)-naphthalenone enantiomer in the desired isomer weight ratio in the resultant isomeric product mixture that allows for the ready recovery of the aforesaid individual isomer therefrom in a highly optically-pure form. This final reaction step is readily accomplished by initially reacting the starting chiral butanoic acid compound obtained in the previous step with the aforesaid thionyl chlorinating agent in an appropriate reaction-inert aprotic organic solvent of choice, in accordance with standard procedure. Preferred reaction-inert aprotic organic solvents of choice for use as proper reaction media in this connection include carbon disulfide, nitrobenzene, various nitroalkanes like nitromethane and nitroethane, aromatic hydrocarbons such as benzene, toluene and xylene, as well as halogenated benzene compounds like o-dichlorobenzene and bromobenzene, in addition to various halogenated lower hydrocarbons such as methylene chloride, ethylene dichloride, trichlorethylene, s-tetrachlorethane and carbon tetrachloride, etc. The starting chiral acid, as previously mentioned, first reacts with the thionyl chloride reagent (that is preferably employed in molar amounts that are in slight excess of those used for the acid starting material) in one of the preferred solvents of choice at temperatures ranging from about 50° C. up to about 85° C. to initially form the corresponding acid chloride in situ, and the resulting reaction mixture containing this intermediate is then slowly cooled to temperatures in the aforesaid temperature range of from about -5° C. up to about 25° C., prior to being treated with a Friedel-Crafts type catalyst in the same type solvent system at a temperature that is maintained within the same range, as aforesaid, until the ring-closure step to finally form the desired chiral final product, viz., (4S)-3,4-dichlorophenyl-3,4-dihydro-1(2H)-naphthalenone, is substantially complete. The preferred solvents for the ring-closure/cyclization reaction are, of course, the same as those used in the initial chlorination reaction. The preferred Friedel-Crafts type catalyst for the ring-closure reaction per se is aluminum chloride, which is preferably employed in an amount that is at least substantially equimolar to that of the thionyl chloride reagent. In a preferred embodiment of this particular step, the molar ratio of stereospecific (4R)-phenylated n-butanoic acid employed as starting material to Friedel-Crafts type catalyst is one that is normally in the range of from about 1.0:1.0 to about 1.0:10.0, with the most preferred ratios ranging from about 1.0:1.0 to about 1.0:2.0. Upon completion of this last reaction step, the desired (4R)-4-(3,4-dichlorophenyl)-3,4-dihydro-1(2H)-naphthalenone compound is readily recovered from the reaction mixture in a conventional manner that is most common to Friedel-Crafts type reactions, viz., by first quenching the reaction mixture with ice, followed by organic extraction of the stirred aqueous medium so obtained with an organic solvent of the same type as originally employed for the reaction (e.g., toluene) and the subsequent isolation of the product from the resulting organic extract, with the latter step preferably being accomplished by means of evaporation under reduced pressure, followed by further purification of the thus-obtained oily residue, preferably via column chromatography over silica gel, etc. In this way, the novel nine-step process of this invention to prepare the new and valuable (4S)-4-(3,4-dichlorophenyl)-1(2H)-naphthalenone compound from the known 3,4-dichlorocinnamyl chloride is now essentially complete.

The 3,4-dichlorocinnamyl chloride starting material required for carrying out the nine-step method of production involved with the overall process of this invention is a known compound which can easily be synthesized by those skilled in the art, starting from common chemical reagents and using conventional methods of organic synthesis. For instance, this particular compound is readily prepared by employing the method of E. A. Steck, as described in *Organic Preparations and Procedures International* (OPPI), Vol. 7, No. 1, p. 3 (1975).

As previously indicated, the (4R)-4-(3,4-dichlorophenyl)-3,4-dihydro-1(2H)-naphthalenone final product afforded by the multi-step process of this invention is a valuable intermediate that ultimately leads to the antidepressant agent known as sertraline or cis-(1S)(4S)-N-methyl-4-(3,4-dichlorophenyl)-1,2,3,4-tetrahydro-1-naphthaleneamine by methods disclosed in the previously discussed prior art. More specifically, (4S)-(3,4-dichlorophenyl)-3,4-dihydro-1(2H)-naphthalenone is first converted to (4R)-N-[4-3(3,4-dichlorophenyl)-3,4-dihydro-1(2H)-naphthalenylidine]methenamine and then finally to the desired cis-(1S)(4R)-N-methyl-4-(3,4-dichlorophenyl)-1,2,3,4-tetrahydro-1-naphthaleneamine by the known methods of the prior art process, as earlier described by W. M. Welch, Jr. et al. in U.S. Pat. No. 4,536,518, as well as in the *Journal of Medicinal Chemistry*, Vol. 27, No. 11, p. 1508 (1984), for the corresponding series of compounds where the starting material is the racemic form of 4-(3,4-dichlorophenyl)-1(2H)-naphthalenone, In the present instance, the optically-active ketone, viz., (4S)-4-(3,4-dichlorophenyl)-1(2H)-naphthalenone, is first reductively aminated to give chiral cis-N-methyl-(3,4-dichlorophenyl)-1,2,3,4-tetrahydro-1-naphthaleneamine, and the latter product is then separated by chromatographic means to ultimately yield the desired final medicinal product which is sertraline. Hence, the novel process of the present invention now provides the new and valuable (4S)-enantiomer known as (4S)-(3,4-dichlorophenyl)-3,4-dihydro-1(2H)-naphthalenone, as discussed above, in pure form and in high yield by a unique nine-step method. This, in turn, allows for a major improvement in the overall synthesis of sertraline by permitting use of the previously-undisclosed asymmetric route, whereby some of the hereinbefore discussed disadvantages of the known prior art method are now largely overcome.

EXAMPLE 1

To a well-stirred solution consisting of 29.5 g (0.1787 mole) of L-(−)-ephedrine dissolved in 40 mL of methylene chloride at 0° C., there are added 20 g (0.0851 mole) of 3,4-dichlorocinnamyl chloride [E. A. Steck, *Organic Preparations and Procedures International* (OPPI), Vol. 7, No. 1, p. 3 (1975)] also dissolved in 40 mL of methylene chloride. Upon completion of this step, the resulting reaction mixture is stirred at room temperature (ca. 20° C.) for a period of one hour and then successively washed with 100 mL of water, 100 mL of aqueous hydrochloric acid (1:2 by volume of 10% hydrochloric acid/water), 100 mL of water and 100 mL of saturated aqueous sodium bicarbonate in that order, followed by drying of the washed organic layer over anhydrous magnesium sulfate. After removal of the drying agent by means of filtration and the solvent by means of evaporation under reduced pressure, there is ultimately obtained a residual yield of crude optically-active unsaturated amide in the form of a foam. Recrystallization of the latter material from isopropyl ether then yields pure chiral N-methyl-N-(β-hydroxy-β-phenylisopropyl)-3-(3,4-dichlorophenyl)propenoamide, m.p. 123°–125° C.

EXAMPLE 2

To a well-stirred solution consisting of 13 g (0.03568 mole) of the chiral α,β-unsaturated amide product of Example 1 dissolved in 500 mL of tetrahydrofuran at −78° C., there are added 106 mL of a 2.02M solution of phenyl magnesium chloride (0.214 mole) in tetrahydrofuran during the course of a 15-minute period. Upon completion of this step, the resulting reaction mixture is allowed to rise in temperature to 0° C. and subsequently stirred at that point for a period of 72 hours. The reaction mixture is next quenched with 260 mL of a phosphate pH 7 buffer, and the resulting gelatinous solids are thereafter collected by means of suction filtration and washed with 260 mL of ethyl acetate. The two phases that form in the filtrate are then separated, and the organic phase is saved and subsequently concentrated in vacuo to afford a residual yield of crude N-methyl-N-(β-hydroxy-β-phenylisopropyl)-3-(3,4-dichlorophenyl)-3-phenylpropanoamide in the form of an off-white paste. This material is used as such in the next reaction step without any further purification really being necessary.

EXAMPLE 3

A well-stirred solution consisting of 16 g (0.0362 mole) of the phenylated amide product of Example 2 dissolved in 169 mL of ethylene glycol which also contains 20.16 g (0.0362 mole) of potassium hydroxide is heated at 100° C. for a period of 48 hours and then stirred at ambient temperature (ca. 20° C.) for a period of one hour. Upon completion of this step, the resulting reaction mixture is diluted with 100 mL of water and the pH of same is subsequently adjusted to pH 10 with 21 mL of added concentrated hydrochloric acid. The resulting aqueous phase is then separated and next extracted with three-130 mL portions of diethyl ether, followed by a pH adjustment of the thus-extracted aqueous phase to pH 2 with 5 mL of concentrated hydrochloric acid. The acidified aqueous phase is next extracted with three-130 mL portions of ethyl acetate, and the combined organic extracts are then washed twice with 30 mL of a phosphate pH 2 buffer and dried over anhydrous magnesium sulfate. After removal of the drying agent by means of suction filtration and the solvent by means of evaporation under reduced pressure, there is eventually obtained a yellow oil as the residue. The latter material is then dissolved in 200 mL of diethyl ether and thereafter washed with two-30 mL fresh portions of phosphate pH 2 buffer. Upon removal of the ether solvent by means of evaporation under reduced pressure, there is ultimately obtained pure 3-(3,4-dichlorophenyl)-(3R)-phenylpropanoic acid, $[\alpha]_D^{25°}$ +3.6° (c=1.0, methylene chloride).

EXAMPLE 4

A solution consisting of 1.17 mL (0.0164 mole) of acetyl chloride dissolved in 100 mL of methanol at 0° C. is stirred at 5° C. for a period of five minutes and then added to 4.4 g (0.0149 mole) of 3-(3,4-dichlorophenyl)-(3R)-phenylpropanoic acid (the product of Example 3), with continued agitation being maintained throughout the course of the addition step. The resulting reaction mixture is then warmed to ambient temperatures and thereafter subjected to constant agitation for a period of 18 hours at room temperature (ca. 20° C.). Upon completion of this step, the solvent is removed by concentrating the solution in vacuo to afford a yellow paste which is then subsequently dissolved in 450 mL of diethyl ether. The resulting ethereal solution is then successively washed with 450 mL of water, 450 mL of a phosphate pH 9 buffer and 450 mL of brine in that order, followed by drying over anhydrous magnesium sulfate. After removal of the drying agent by means of filtration and the solvent by means of evaporation under reduced pressure, there is eventually obtained a crude yellow residual oil which is subsequently chromatographed on a silica gel column to yield pure methyl 3-(3,4-dichlorophenyl)-(3R)-phenylpropanoate in the form of a colorless oil, $[\alpha]_D^{25°}$ +1.6° (c=1.062, methylene chloride).

EXAMPLE 5

A solution consisting of 2.54 g (0.0082 mole) of methyl 3-(3,4-dichlorophenyl)-(3R)-phenylpropionate (the product of Example 4) dissolved in 25 mL of tetrahydrofuran is added to a well-stirred slurry consisting of 561 mg. (0.01479 mole) of lithium aluminum hydride suspended in 25 mL of tetrahydrofuran, with the temperature always being maintained below 35° C. throughout the course of the additional step. After stirring for a period of one hour at 20° C., an additional 186 mg-portion of lithium aluminum hydride is next added and the resulting reaction mixture is thereafter subjected to constant agitation at room temperature (ca. 20° C.) for a period of 18 hours. Upon completion of this step, the stirred reaction mixture is successively quenched with 0.380 mL of water, 0.380 mL of 15% aqueous sodium hydroxide and 1.14 mL of water in that order. The quenched reaction mixture is then filtered through magnesium sulfate, and the resulting filtrate is subsequently concentrated in vacuo to give a clear colorless oil. Further purification of the latter material by means of column chromatography over silica gel then yields pure 3-(3,4-dichlorophenyl)-(3R)-phenylpropanol in the form of a colorless oil, $[\alpha]_D^{25°}$ −4.82° (c=1.059, methylene chloride).

EXAMPLE 6

A well-stirred solution consisting of 1.28 g (0.00455 mole) of 3-(3,4-dichlorophenyl)-(3R)-phenylpropanol (the product of Example 5) and 1.44 g (0.00546 mole) of triphenylphosphine dissolved in 3 mL of carbon tetrachloride is heated at 80° C. for a period of three hours. Upon completion of this step, the resulting reaction mixture is cooled to room temperature (ca. 20° C.) and then diluted with 200 mL of 5% aqueous sodium sulfate, followed by further dilution with 200 mL of chloroform. The organic layer is then separated, and the resulting aqueous phase is next extracted with two-200 mL portions of fresh chloroform. The three-separate organic extracts are then combined and subsequently dried over anhydrous magnesium sulfate. After removal of the drying agent by means of filtration and the solvent by means of evaporation under reduced pressure, there is eventually obtained a crude colorless oil as the residue. Purification of the latter material by means of column chromatography over silica gel then yields pure 3-(3,4-dichlorophenyl)-(3R)-phenylpropyl chloride, $[\alpha]_D^{25°} -1.8°$ (c=0.95, methylene chloride).

EXAMPLE 7

A well-stirred solution consisting of 1.25 g (0.00417 mole) of 3-(3,4-dichlorophenyl)-(3R)-phenylpropyl chloride (the product of Example 6), 543 mg (0.00834 mole) of potassium cyanide and 110 mg (0.00042 mole) of 1,4,7,10,13,16-hexaoxacyclooctadecane all dissolved in 17 mL of acetonitrile is stirred under a nitrogen atmosphere at 85° C. for a period of 18 hours. Upon completion of this step, the reaction mixture is cooled to room temperature (ca. 20° C.), diluted with 100 mL of water and then extracted with two-100 mL portions of chloroform. The combined organic extracts are next washed with 100 mL of brine and finally concentrated in vacuo to give an oil. Purification of the latter material by means of column chromatography on silica gel then yields pure 4-(3,4-dichlorophenyl)-(4R)-phenylbutyronitrile, $[\alpha]_D^{25°} +1.6°$ (c=1.06, methylene chloride).

EXAMPLE 8

A well-stirred solution consisting of 602 mg (0.00206 mole) of 4-(3,4-dichlorophenyl)-(4R)-phenylbutyronitrile (the product of Example 7) dissolved in 6 mL of ethylene glycol containing 1.17 g (0.0206 mole) of potassium hydroxide is heated at 100° C. for a period of 18 hours. The resulting reaction mixture is then cooled to room temperature (ca. 20° C.), diluted with 150 mL of water and the pH of the diluted aqueous mixture is subsequently adjusted to pH 11 with concentrated sulfuric acid. The resulting aqueous solution is then extracted with two-100 mL portions of diethyl ether, followed by an adjustment of the thus-extracted aqueous phase to pH 2 with additional concentrated sulfuric acid. The acidified aqueous phase is next extracted with three-100 mL portions of diethyl ether, and the combined organic extracts are thereafter washed with 100 mL of a phosphate pH 2 buffer. Removal of the solvent from the washed organic extracts, via concentration under reduced pressure, then yields an amber oil as the final residual product. In this manner, there is ultimately obtained pure 4-(3,4-dichlorophenyl)-(4R)-phenylbutanoic acid, 3.6° (c=1.00, chloroform).

EXAMPLE 9

A well-stirred solution consisting of 570 mg (0.00184 mole) of 4-(3,4-dichlorophenyl)-(4R)-phenylbutanoic acid (the product of Example 8) dissolved in 2.6 mL of toluene is heated under a nitrogen atmosphere at 65° C., while 0.175 mL (0.0024 mole) of thionyl chloride is slowly thereto in a dropwise manner. The resulting reaction solution is thereafter stirred at 65° C. for a period of 2.5 hours and finally cooled to room temperature (ca. 20° C.). Upon completion of this step, the solvents are next removed from the organic solution by means of distillation in vacuo to give an amber oil which is then subsequently chased with two-1.8 mL portions of fresh toluene.

The above-obtained residual oil (consisting essentially of pure 4-(3,4-dichlorophenyl)-(4R)-phenylbutanoyl chloride) is then dissolved in 0.5 mL of toluene and thereafter added as such in a dropwise manner to a well-stirred suspension of 320 mg (0.0024 mole) of aluminum chloride in 2.6 mL of toluene, while the temperature is maintained at 0°-5° C. throughout the course of the addition step. After stirring at ambient temperatures for a period of 40 minutes, the final reaction mixture is then quenched onto ice (3.6 g) and thereafter stirred for a period of ca. 16 hours. The aqueous solution so obtained is next extracted with 2 mL of toluene and the resulting organic layer is then separated, washed with a phosphate pH 12 buffer and subsequently dried over anhydrous magnesium sulfate. After removal of the drying agent by means of suction filtration and the solvent by means of evaporation under reduced pressure, there is eventually obtained a light yellow oil as the residual product. Purification of the latter material by means of column chromatography over silica gel then yields (4S)-4-(3,4-dichlorophenyl)-3,4-dihydro-1(2H)-naphthalenone as a white crystalline solid, $[\alpha]_D^{25°}$ C. $+37.9°$ (c=1.02 acetone). The latter value corresponds to a 79:21 ratio of enantiomers or an optical purity of 58% when expressed in terms of the percent amount of enantiomeric excess (% ee).

I claim:

1. A process for preparing the (4S)-enantiomer of 4-(3,4-dichlorophenyl)-3,4-dihydro-1(2H)-naphthalenone in a highly optically-pure form, starting from 3,4-dichlorocinnamyl chloride, which comprises the sequential series of steps that involve:

(a) first reacting 3,4-dichlorocinnamyl chloride with at least an equimolar amount of L-(−)-ephedrine in a chlorinated lower hydrocarbon solvent at a temperature ranging from about −20° C. up to about 25° C. to form the corresponding chiral N-methyl-N-(β-hydroxy-β-phenylisopropyl)-3-(3,4-dichlorophenyl)propenoamide;

(b) subjecting the chiral unsaturated amide product obtained in step (a) to a Grignard reaction with a large excess in moles of phenyl magnesium chloride or bromide in a cyclic or lower dialkyl ether at a temperature ranging from about −80° C. up to about 25° C., followed by hydrolysis, to effect a conjugate addition of the phenyl group and the hydrogen element to the aforesaid α,β-propenoamide and so selectively form the corresponding chiral N-methyl-N-(β-hydroxy-β-phenylisopropyl)-3-(3,4-dichlorophenyl)-3phenylpropanoamide;

(c) hydrolyzing the aforesaid chiral 3-phenylated propanoamide product of step (b) in a lower alkylene glycol solvent in the presence of an alkali metal hydroxide as base to form the corresponding 3-(3,4-dichlorophenyl)-(3R)-phenylpropanoic acid;

(d) esterifying the stereospecific (3R)-phenylated propanoic acid obtained in step (c) with an appropriate lower alkanol in the presence of thionyl chloride or a lower alkanoyl chloride to form the corresponding lower alkyl 3-(3,4-dichlorophenyl)-(3R)-phenylpropanoate;

(e) reducing the stereospecific (3R)-phenylated propanoic acid ester of step (d) with an appropriate carbonyl reducing agent in a reaction-inert polar aprotic organic solvent at a temperature ranging from about 0° C. up to about 100° C. until the reduction to form the corresponding desired 3-(3,4-dichlorophenyl)-(3R)-phenylpropanol intermediate is substantially complete;

(f) chlorinating the stereospecific phenylated n-propanol compound obtained in step (e) with carbon tetrachloride in an excess of said reagent as solvent and in the presence of triphenylphosphine at a temperature ranging from about 50° C. up to about the reflux temperature of the reaction mixture to form the corresponding 3-(3,4-dichlorophenyl)-(3R)-phenylpropyl chloride;

(g) reacting the stereospecific (3R)-phenylated n-propyl chloride obtained in step (f) with an alkali metal cyanide in a reaction-inert polar organic solvent at reflux temperatures to form the corresponding 4-(3,4-dichlorophenyl)-(4R)-phenylbutyronitrile;

(h) hydrolyzing the stereospecific (4R)-phenylated butyronitrile product of step (g) in a lower alkylene glycol solvent in the presence of an alkali metal hydroxide as base to form the corresponding 4-(3,4-dichlorophenyl)-(4R)-phenylbutanoic acid; and (i) thereafter converting the stereospecific (4R)-phenylated n-butanoic acid compound obtained in step (h) to the corresponding 4-(3,4-dichlorophenyl)-(4R)-phenylbutanoyl chloride by treatment with thionyl chloride in a reaction-inert aprotic organic solvent, followed by cyclization of the aforesaid butanoyl chloride compound in the presence of a Friedel-Crafts type catalyst at a temperature ranging from about −5° C. up to about 25° C. to finally yield the corresponding(4S)-4-(3,4-dichlorophenyl)-3,4-dihydro-1(2H)-naphthalenone enantiomer in the desired isomer weight ratio in the resultant isomeric product mixture that allows for the ready recovery of said individual isomer therefrom in a highly optically-pure form.

2. A process as claimed in claim wherein the chlorinated lower hydrocarbon solvent employed in step (a) is methylene chloride.

3. A process as claimed in claim 1 wherein the Grignard reagent employed in step (b) is phenyl magnesium chloride.

4. A process as claimed in claim wherein the ethereal solvent employed in step (b) is tetrahydrofuran or diethyl ether.

5. A process as claimed in claim 1 wherein the glycol solvent employed in both steps (c) and (h) is ethylene glycol and the alkali metal hydroxide is potassium hydroxide.

6. A process as claimed in claim 1 wherein the lower alkanol employed in step (d) is methanol and the lower alkanoyl chloride is acetyl chloride.

7. A process as claimed in claim wherein the carbonyl reducing agent employed in step (e) is an alkali metal aluminum hydride.

8. A process as claimed in claim 7 wherein the alkali metal aluminum hydride is lithium aluminum hydride.

9. A process as claimed in claim wherein the aprotic organic solvent employed in step (e) is tetrahydrofuran.

10. A process as claimed in claim 1 wherein the reduction in step (e) is conducted at a temperature ranging from about 15° C. up to about 30° C.

11. A process as claimed in claim 1 wherein the chlorination reaction in step (f) is conducted at the reflux temperature of the reaction mixture.

12. A process as claimed in claim wherein the reaction-inert aprotic organic solvent employed in step (g is acetonitrile.

13. A process as claimed in claim wherein the reaction-inert aprotic organic solvent employed in step (i) is an aromatic hydrocarbon solvent.

14. A process as claimed in claim 13 wherein the aromatic hydrocarbon solvent is toluene.

15. A process as claimed in claim 1 wherein the Friedel-Crafts-type catalyst employed in step (i) is aluminum chloride.

* * * * *